United States Patent [19]

LaForest et al.

[11] Patent Number: 4,605,412
[45] Date of Patent: Aug. 12, 1986

[54] MAMMARY PROSTHESIS HAVING ADJUSTABLE PROJECTION

[75] Inventors: Lance J. LaForest, Scottsdale, Ariz.; Rita L. Taylor, Racine, Wis.

[73] Assignee: Medical Engineering Corp., Racine, Wis.

[21] Appl. No.: 672,785

[22] Filed: Nov. 19, 1984

Related U.S. Application Data

[63] Continuation-in-part of Ser. No. 459,383, Jan. 20, 1983, abandoned.

[51] Int. Cl.$^4$ .................................................. A61F 2/12
[52] U.S. Cl. ......................................... 623/8; 128/1 R
[58] Field of Search ............... 3/36, 1; 128/1 R, 462, 128/489, 117, 118, 89 R, 85

[56] References Cited

U.S. PATENT DOCUMENTS

| | | | |
|---|---|---|---|
| 2,636,182 | 4/1953 | Freedman | 2/267 |
| 3,600,718 | 8/1971 | Boone | 3/36 |
| 3,852,833 | 12/1974 | Koneke et al. | 623/7 |
| 4,253,201 | 3/1981 | Ross et al. | 3/36 |
| 4,298,997 | 11/1981 | Rybka | 3/36 |
| 4,298,998 | 11/1981 | Naficy | 3/36 |

FOREIGN PATENT DOCUMENTS 7232014 5/1974 France .

OTHER PUBLICATIONS

Radovan "Subcutaneous Tissue Expander", Heyer-Schulte Co., publication.
Sales literature–"Surgitek" Medical Engineering Corp., Racine, Wisconsin.
Sales literature–"Surgitek Bilumen Mammary Prosthesis" Medical Engineering Corp., Racine, Wisconsin.
"Augmentation Mammoplasty", Nursing, Feb. 1979, pp. 60–64.

Primary Examiner—Richard J. Apley
Assistant Examiner—David Isabella
Attorney, Agent, or Firm—Quarles & Brady

[57] ABSTRACT

An adjustable mammary prosthesis for augmentation mammoplasty is comprised of an outer teardrop-shaped, gel filled distensible container or shell. Disposed within the outer shell is an extensible column-shaped container with a valve. The projection ($H_1$) of the prosthesis can be altered without altering the base diameter (B) of the prosthesis by adding an appropriate volume of fluid to the column-shaped container via the valve to extend it axially and to increase its height and the projection ($H_2$) of the outer container. In another embodiment, a pillow-shaped distensible inner container is positioned between the top of the extensible column-shaped inner container and the underside of the top of the outer container.

4 Claims, 5 Drawing Figures

MAMMARY PROSTHESIS HAVING ADJUSTABLE PROJECTION

RELATED CASE

The present application is a continuation-in-part of our earlier application Ser. No. 459,383 filed Jan. 20, 1983 now abandoned.

FIELD OF THE INVENTION

This invention relates generally to the field of medical implants and, more particularly, to mammary prostheses.

BACKGROUND OF THE INVENTION

Augmentation mammoplasty, that is, surgical augmentation of the breasts, is a common cosmetic surgical procedure that has been performed for many years. This procedure usually entails making a surgical incision to create a pocket in the breast and then inserting a mammary prosthesis, generally shaped similar to the human breast, into the pocket.

Mammary prostheses are well known in the art and generally take several forms. There are single unitary mammary prostheses which comprise a shell of physiologically inert material, such as silicone rubber or the like which are filled with a silicone gel or a saline solution and then sealed. Inflatable mammary prostheses are also available and generally include a hollow shell of physiologically inert material such as silicone rubber which is filled with a saline solution during surgery to achieve the appropriate prosthesis and breast size. In addition to the single shell inflatable mammary prosthesis, an inflatable bilumen or double shell mammary prosthesis is also available. The inflatable bilumen mammary prosthesis generally includes an inner gel implant filled within silicone gel and then sealed. The inner gel implant is disposed within a partially fluid filled, inflatable shell that is further filled through a valve with a saline solution during surgery to achieve the desired breast augmentation.

Both the single shell inflatable mammary prosthesis and the inflatable bilumen mammary prosthesis advantageously permit the size and, in particular, the projection or height of the mammary prosthesis to be varied by altering the amount of fluid admitted to the prosthesis. However, admitting additional fluid into the prosthesis to increase the mammary prosthesis projection also results in an increase in the mammary prosthesis base diameter, which may be very undesirable. Increasing the mammary prosthesis base dimension once the prosthesis has been inserted may cause tearing of the tissue and possible bleeding. While the projection of the single shell inflatable mammary prosthesis and the inflatable bilumen mammary prosthesis can be varied slightly by the addition of fluid to the prosthesis without severely altering the base dimension of the prosthesis, to obtain a significant increase in the prosthesis projection, it is necessary to employ a prosthesis having a larger molded shell.

BRIEF SUMMARY OF THE INVENTION

In contrast to the prior art mammary prosthesis whose projection may not be significantly increased without a corresponding increase in the prosthesis base dimension, the present invention concerns an improved mammary prosthesis whose projection can be significantly increased without altering the prosthesis base dimension. The mammary prosthesis of the present invention comprises a distensible outer fluid container filled with a physiologically inert non-compressible fluid, an extensible inner column shaped partially filled fluid container disposed within said outer container and a valve in communication with said inner container for admitting additional quantities of fluid into said inner container to preferentially extend said inner container vertically and increase its height so as to deform said outer container and to increase the projection of the outer container.

In one preferred embodiment of the invention, an improved, adjustable basis mammary prosthesis comprises a physiologically inert outer container which is formed of a tear-drop shaped shell whose opening is sealed by a disc. Prior to filling the outer container with a physiologically inert fluid, such as silicone gel, a pillow shaped, physiologically inert, fluid filled container is disposed within the outer container beneath the top of the interior surface and is supported from the disc by a vertically extensible, partially fluid filled, column shaped container adhered at its bottom to the disc. A valve is disposed through the disc in communication with the column shaped container to allow an inert fluid, such as a silicone gel, to be admitted into the column shaped container. The addition of more fluid into the column shaped container causes the column shaped container to extend vertically to urge the pillow shaped container against the outer shell so as to deform the outer shell and increase the mammary prosthesis projection.

Alternatively, the mammary prosthesis of the present invention can be constructed of a hollow tear-drop shaped container whose opening is sealed by a disc as before. A single, partially fluid filled, column shaped vertically extensible container is disposed within the interior of the outer shell so as to be beneath, but not in contact with the top interior surface of the outer container. A valve communicates through the outer container with the inner container so that additional fluid can be admitted to the inner container. When additional fluid is admitted into the inner column shaped container, the column shaped container extends axially to vertically deform the outer container, thereby increasing the prosthesis projection without altering the prosthesis base dimension.

It is an object of the present invention to provide an improved mammary prosthesis having an adjustable projection.

It is yet another object of the present invention to provide an improved mammary prosthesis whose projection can be significantly increased without altering the prosthesis base dimension.

BRIEF DESCRIPTION OF THE DRAWINGS

The features of the invention believed to be novel are set forth with particularity in the appended claims. However, the invention itself, both as to organization and method of operation, together with further objects and advantages thereof may best be understood by reference to the following description taken in conjunction with the accompanying drawings in which:

DETAILED DESCRIPTION OF PREFERRED EMBODIMENT

Figure 1:
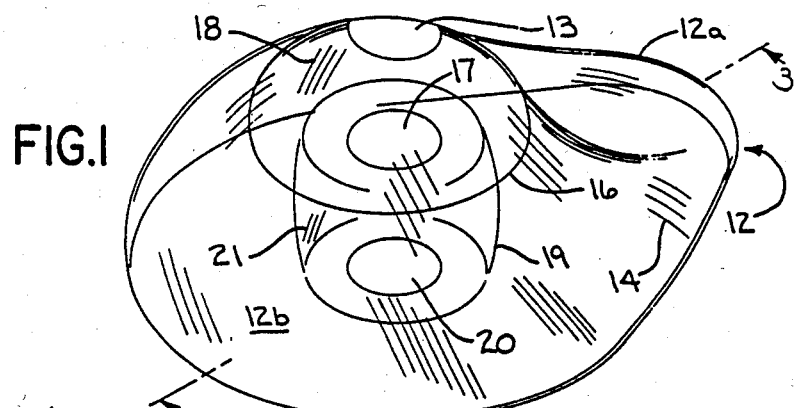
FIG. 1 is a perspective view of a preferred embodiment of a mammary prosthesis having an adjustable basis.
Figure 2:
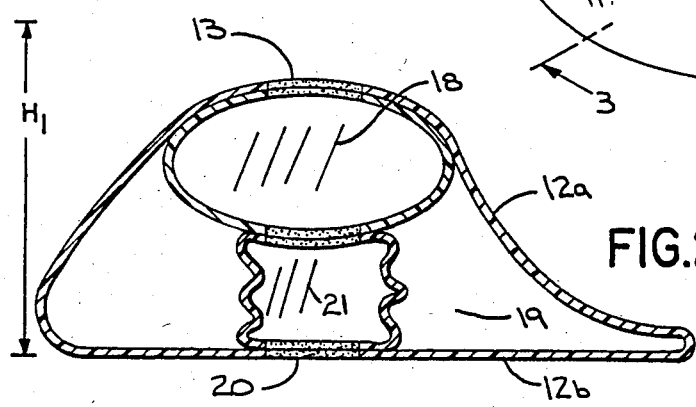
FIG. 2 is a cross-sectional view of the mammary prosthesis of FIG. 1 in its semi-inflated state.
Figure 3:
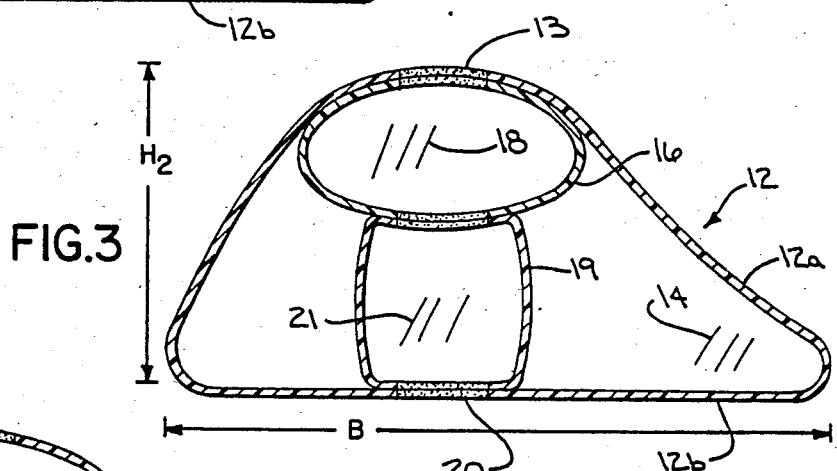
FIG. 3 is a cross-sectional view of the mammary prosthesis of FIG. 1 in its inflated state.

Referring now to the Figures, an improved mammary prosthesis 10 is illustrated in perspective view in FIG. 1 and is shown in cross sectional elevation in its semi-inflated and inflated states in FIGS. 2 and 3, respectively. Prosthesis 10 is comprised of a distensible container 12 configured of a shell or envelope 12a whose opening is sealed by a disc 12b. Both shell 12a and disc 12b are manufactured from a physiologically inert (safe), elastomeric, material such as silicone rubber or the like. Shell 12a, which typically has relatively thick interior walls, may have either a teardrop shape as illustrated or a round or hemispherical shape depending on the desired mammary augmentation. The interior void of shell 12a is filled through a seal 13 located at the uppermost part of the shell 12a with physiologically inert non-compressible fluid 14, such as dextran, saline, or a silicone gel. Generally, silicone gel is preferred, because when shell 12a is filled with silicone gel 14, the resulting prosthesis allows a mammary augmentation which is more natural in appearance and behavior than would be achieved with a saline or dextran filled shell Disposed within the void of shell 12a prior to filling with gel 14 is an interior container 16 which, like shell 12a and disc 12b, is constructed of an inert, physiologically safe, elastomeric material such as silicone rubber. Unlike shell 12a, which has relatively thick walls, container 16, which is typically pillow-shaped, has relatively thin walls allowing container 16 to be extremely pliable which, as will be explained hereinafter, enables the projection of the prosthesis 10 to be adjusted. Container 16 is provided with a valve 17 at its bottom through which a physiologically inert fluid 18, such as such as silicone gel, is admitted into the container.

Container 16 is supported from disc 12b within the void of shell 12a beneath seal 13 so as to be beneath the "tear drop" of shell 12a by another interior container 19, which is typically column shaped. Container 19, like container 16, is configured of an inert, physiologically safe, elastomeric material such as silicone rubber. Like shell 12a, the walls of container 19 are relatively thick. A valve 20, typically a cylinder valve, is disposed through disc 12b in communication with the bottom of shell 19 to enable fluid such as silicone gel 21 to be admitted into the interior hollow of the container.

In practice, container 19 is initially filled with a small volume of silicone gel 21 through valve 20 so that the total height of container 16 and the partially collapsed container 19 equals the projection $H_1$, that is to say, the height of shell 12a as illustrated in FIG. 2. During surgery, the projection of prosthesis 10 can be increased to $H_2$ by expanding container 19 along its axis by the admission of a saline solution 22 into container 19 through valve 20 so as to urge container 16 upwardly against the interior wall of shell 12a, as illustrated in FIG. 3. As container 16 is urged against the interior of shell 12a by container 19, the shell 12a is deformed so as to increase the shell projection. As can now be appreciated, the pliability of container 16, as a consequence of its relatively thin walls, permits the outer shell 12a to be more evenly deformed which is very desirable.

In contrast to a prior art inflatable mammary prothesis whose base dimension is likely to be altered when the prosthesis projection is altered by increasing the outer shell volume through the addition of more fluid into the outer shell, the projection, of the mammary prothesis 10 of the present invention can be increased without any increase in the base dimension B of the prothesis as illustrated in FIG. 3. When the column shaped container 19 is filled with a volume of saline fluid 22 to urge the pillow-shaped container 16 against the interior surface of shell 12a to deform the shell, the overall volume of shell 12a is not substantially increased. Rather, only the height or projection of the shell 12a changes. Since the shell volume does not substantially change, the shell base dimension B does not change significantly.

The ability of prosthesis 10 to exhibit a substantially constant base dimension notwithstanding adjustments to its projection is very advantageous. Generally, the base dimension for an implant is selected in accordance with the diameter of the breast to be augmented. If the base dimension is unknowingly altered by virtue of prosthesis inflation, as will likely occur with prior art mammary prostheses when attempts are made to increase the prosthesis projection by the addition of fluid into the outer shell, then it is likely that resultant augmentation may not appear natural.

Mammary prosthesis 10 is readily constructed in the following manner. First, the column-shaped container 19 is partially filled with gel 21 through valve 20 and the valve is then closed. The pillow-shaped container 16 is then adhered to the top of container 19 so that seal 17 is in contact with container 19 and container 16 is thereafter filled with silicone gel. Next, both containers 16 and 19 are debubbled and then baked to cure or vulcanize the silicone gel within each container.

Following the step of baking, the sub-assembly of the column container 19 and pillow-shaped container 16 are then disposed within the inside of the outer shell 12a so as to be beneath seal 13 and then the column shaped container 19 is adhered to disc 12b. After containers 16 and 19 are disposed within shell 12a and container 19 is adhered to disc 12b, the disc 12b is secured to shell 12a. The resultant structure is then baked. Thereafter, shell 12a and container 19 are filled with silicone gel, and then the entire prosthesis is debubbled and then baked. Finally, the valve 20 is itself filled with silicone gel and is sealed so that the prosthesis is now ready for subsequent use.

Figure 4:
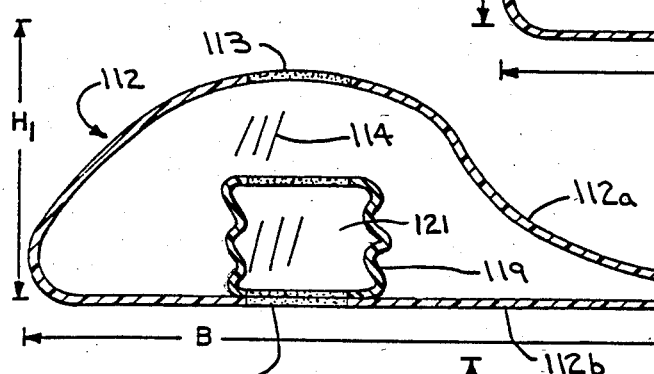
FIG. 4 is a cross-sectional view of an alternate preferred embodiment of a mammary prosthesis shown in its semi-inflated state.
Figure 5:
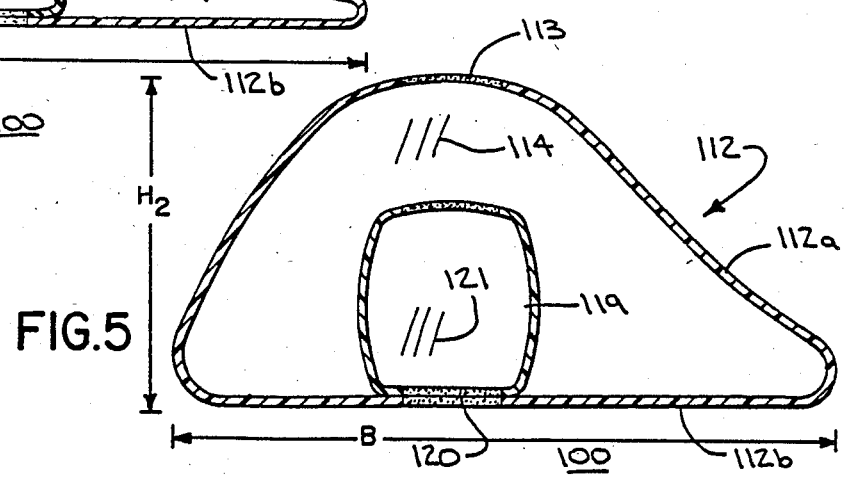
FIG. 5 illustrates the mammary prosthesis of FIG. 4 in its inflated state.

An alternate preferred embodiment 100 of a mammary prosthesis having an adjustable basis is illustrated in cross sectional elevation in its semi-inflated and its inflated states in FIGS. 4 and 5, respectively. Prosthesis 100, like prosthesis 10, is comprised of a hollow extensible container 112, typically teardrop in shape, the container being configured of a shell 112a made from an elastomeric inert material such as silicone rubber, and an elastomeric, 112b which seals the opening into shell 112a. At the top of shell 112a that is, directly beneath the "tear drop" of shell 112a, is a seal 113 which allows an inert fluid 114, typically a silicone gel, to be admitted into the void of shell 112a. Prior to adhering disc 112a to shell 112a and filling the shell with an inert fluid 114, an inner axially extensible container 119, typically comprised of a column-shaped elastomeric shell 119, is adhered to disc 112b so as to be directly beneath seal 113 of shell 112a. A valve 120 is disposed through disc 112B so as to be in communication with column shaped container 119 for admitting an inert fluid 121, such as silicone gel, into container 119 so that the container is partially filled.

The projection or height $H_1$ of prosthesis 100 in its semi-inflated state, illustrated in FIG. 4, may be readily increased to $H_2$ as illustrated in FIG. 4 during augmentation mammoplasty by admitting saline fluid or the like into container 119 through valve 120 so that the container extends along its axis so as to deform envelope 112a vertically, as illustrated in FIG. 5, thereby increasing the prosthesis projection. The base dimension B of prosthesis 100 remains substantially the same notwithstanding the addition of further fluid into container 119 because, as the container 119 extends along its vertical axis, shell 112a is deformed vertically as opposed to horizontally. In comparison with prosthesis 10 described with respect to FIGS. 1 and 2, prosthesis 100 is all but identical except that prosthesis 100 obviates the need for an interior pillow shaped container such as pillow shaped container 16 of FIGS. 1, 2 and 3. Thus, prosthesis 100 of FIGS. 4 and 5 is less expensive to fabricate and manufacture than prosthesis 10 of FIGS. 1, 2 and 3.

Prosthesis 100 is constructed in a manner very much similar to the construction of prosthesis 10 described earlier. However, owing to the lack of any pillow shaped container within the prosthesis, the steps of adhering the pillow shaped container to the column shaped container and filling the pillow shaped container with silicone gel are thus not required.

The foregoing describes an improved mammary prosthesis whose projection can be readily adjusted by inflating an inner shell within the prosthesis without altering the prosthesis base dimension.

While only certain preferred features of the invention have been shown by way of illustration, many modifications and changes will occur to those skilled in the art. For example, while the container 19 has been shown as a collapsed container of defined volume in its partially-filled state, it could also take the form of a container which extends preferentially along its vertical axis. It is, therefore, to be understood that the appended claims are intended to cover all such modifications and changes as fall within the true spirit of the invention.

We claim:

1. An improved prosthesis having a vertical axis defining a projection ($H_1$) which is adjustable without increasing the prosthesis base (B) dimension comprises:
   a first distensible outer container having a substantially fixed base dimension;
   a second column shaped contained having a flat top disposed within the interior of said first container and wherein a longitudinal axis of said column shaped contained is aligned substantially parallel to said vertical axis, the interior of said second container being partially filled with silicone gel and the remainder of the interior of said first container being completely filled with silicone gel; and
   means for adding liquid to the silicone gel in the second container to further fill said prosthesis thereby extending said column shaped container vertically along said longitudinal axis thus vertically increasing said projection of said prosthesis without increasing said base dimension of said first container.

2. An improved prosthesis of claim 1 wherein a third container for fluid is disposed on the top of the second container inside the first container.

3. A prosthesis of claim 1 wherein the first container has a shell of physiologically inert material.

4. A prosthesis of claim 1 in which the liquid is saline solution.

* * * * *

UNITED STATES PATENT AND TRADEMARK OFFICE
CERTIFICATE OF CORRECTION

PATENT NO. : 4,605,412

DATED : August 12, 1986

INVENTOR(S) : LaForest, et al.

It is certified that error appears in the above-identified patent and that said Letters Patent is hereby corrected as shown below:

Column 6, line 15, "contained" should read --container--

Column 6, line 18, "contained" should read --container--

Signed and Sealed this

Eleventh Day of November, 1986

Attest:

DONALD J. QUIGG

*Attesting Officer*  *Commissioner of Patents and Trademarks*